(12) United States Patent
Rahmouni et al.

(10) Patent No.: US 7,091,509 B2
(45) Date of Patent: Aug. 15, 2006

(54) METHOD FOR DETERMINING AT LEAST ONE ENERGETIC PROPERTY OF A GAS FUEL MIXTURE BY MEASURING PHYSICAL PROPERTIES OF THE GAS MIXTURE

(75) Inventors: Camal Rahmouni, Nantes (FR);
Mohand Tazerout, Carquefou (FR);
Olivier Le Corre, Saint-Herblain (FR)

(73) Assignee: Dalkia France, Saint-Andre (FR)

( * ) Notice: Subject to any disclaimer, the term of this patent is extended or adjusted under 35 U.S.C. 154(b) by 140 days.

(21) Appl. No.: 10/484,820

(22) PCT Filed: Jul. 30, 2002

(86) PCT No.: PCT/FR02/02739

§ 371 (c)(1),
(2), (4) Date: Jan. 30, 2004

(87) PCT Pub. No.: WO03/012435

PCT Pub. Date: Feb. 13, 2003

(65) Prior Publication Data

US 2004/0195531 A1    Oct. 7, 2004

(30) Foreign Application Priority Data

Jul. 30, 2001    (FR) .................................. 01 10197

(51) Int. Cl.
*G01N 15/06*    (2006.01)

(52) U.S. Cl. .................................. 250/573; 250/222.2
(58) Field of Classification Search ................ 250/573, 250/222.2
See application file for complete search history.

(56) References Cited

U.S. PATENT DOCUMENTS

| 4,594,510 A | 6/1986 | Brown et al. |
| 5,103,181 A | 4/1992 | Gaisford et al. |
| 6,536,946 B1 * | 3/2003 | Froelich et al. ............... 374/36 |

FOREIGN PATENT DOCUMENTS

| EP | 959354 | 11/1999 |
| FR | 2543687 | 10/1984 |
| RU | 2051318 | 12/1995 |
| WO | 00/11465 | 8/1999 |

* cited by examiner

*Primary Examiner*—Que T. Le
(74) *Attorney, Agent, or Firm*—Dennison, Schultz, Dougherty & MacDonald

(57) ABSTRACT

The present invention relates to a method of determining at least one energy property of a gaseous mixture which consists in:
1. measuring, on said gaseous mixture, n physical properties $\phi_i$ at a temperature T and/or one physical property $\phi_i$ at n different temperatures;
2. determining, from said physical properties, the composition of a gas with n+1 components that is equivalent to said mixture; and
3. deducing the energy properties of said gaseous mixture from said composition of the equivalent gas.

12 Claims, 2 Drawing Sheets

METHOD FOR DETERMINING AT LEAST ONE ENERGETIC PROPERTY OF A GAS FUEL MIXTURE BY MEASURING PHYSICAL PROPERTIES OF THE GAS MIXTURE

This application is a filing under 35 USC 371 of PCT/FR02/02739, filed Jul. 30, 2002.

BACKGROUND OF THE INVENTION

The present invention relates to a method of determining at least one energy property of a gaseous fuel mixture by measuring physical properties of the gaseous mixture, determining the composition of a gas equivalent to said gaseous mixture and deducing the energy properties from said composition.

The energy properties of a gas, such as the calorific value, the Wobbe index, the stoichiometric air/fuel ratio or the methane index, are of great industrial interest. In fact, a variation in the composition of a gas (for example natural gas) due to there being a large number of sources of supply (Algerian gas, Norwegian gas, Russian gas, etc.) can cause serious damage in stationary gas engines. These engines are generally used for the simultaneous production of heat and electricity (cogeneration). Furthermore, the efficient use of gaseous fuels in internal combustion engines depends mainly on their ignition properties and combustion properties.

The energy property which makes it possible to follow the variations in the quality of natural gas in terms of the antiknock value is the methane index.

Fuel gases, which are of relative importance in terms of the very different energy properties, also have diverse origins: wood gas, coal gas, natural gas, etc.

When biogas is used to drive internal combustion engines, a variation in the composition of the gas can have serious effects on the performance characteristics of the engine. For example, there can be power fluctuations due to the variation in net calorific value (the NCV can vary from 10 to 25 MJ/m³). Thus, for optimal operation of the engine, it becomes essential to measure the NCV of the biogas.

The Wobbe index is another important energy property of gaseous fuels (it can vary from 10 to 30 MJ/m³). It is an important criterion of the interchangeability of gases in engines. A variation in composition does not cause an appreciable change in the air factor or the combustion rate if the Wobbe index remains almost constant. This index can be deduced from calculation of the calorific value by means of the following relationship:

$$W = \frac{NCV}{\sqrt{d}} \quad (1)$$

where NCV is the net calorific value of the gas and d is the density of the gas.

The quality of gaseous fuels can be measured by numerous techniques, among which there may be mentioned the techniques of measuring the calorific value and the technique of measuring the methane index.

a) Methods of Measuring the Calorific Value

Given the composition of a gaseous mixture, it is easy to calculate its calorific value by using the specific value of each of the constituents of the gas in question.

Direct determination of the calorific value can be effected by means of hand-operated calorimeters and automatic calorimeters, for example the bomb calorimeter, Junkers calorimeters and the Union microcalorimeter.

These traditional methods are cumbersome, expensive and difficult to carry out when it is desired to find out the calorific value of a gaseous mixture within an operating plant.

The method of calculating the calorific value described in international patent application WO 99/36767 considers the measurement of two physical properties (the speed of sound and the thermal conductivity). This method was developed using natural gases representative of the whole range of gases encountered in the gas distribution system in Great Britain. The laboratory experiments performed with these natural gases made it possible to determine the speed of sound in these gases and then to correlate these results with the calorific value. As a single property is not sufficient to follow the variations in calorific value according to whether the gases do or do not have a significant content of inert components, a second physical property (the thermal conductivity) was combined with the speed of sound. According to this method the calorific value is deduced by means of the following correlation:

$$CV = a \cdot ThC_H + b \cdot ThC_L + c \cdot SoS + d \cdot T_a + e \cdot T_a^2 + f \quad (2)$$

in which:
CV is the calorific value;
$ThC_H$ is the thermal conductivity at temperature $T_H$;
$ThC_L$ is the thermal conductivity at temperature $T_L$;
SoS is the speed of sound at ambient temperature;
$T_a$ is the ambient temperature of the gas;
a, b, c, d, e and f are constants.

The constants were determined by means of a regression obtained on gas samples of different origins in Great Britain. However, this method only uses gases representative of the gases distributed in Great Britain and cannot therefore be generalized.

A second method of determining the calorific value is based on a knowledge of the content of nitrogen and carbon dioxide in the gas, as well as the value of the density of this gas. The proposed relationship was used by Candwell (1967) and is only valid for gases with a Wobbe index of between 43.4 and 44.4 MJ.m⁻³ (Groningue gas):

$$CV = 5.671 + 61.38d - 98.97K_{CO2} - 64.57K_{N2} \quad (3)$$

where $K_{CO2}$ is the carbon dioxide fraction and $K_{N2}$ is the nitrogen fraction in the gas.

However, these last two methods are not applicable to all the gases distributed in Europe.

b) Methods of Measuring the Methane Index

Experimental Determination of the Methane Index

The methane index is generally measured on a CFR/RDH (Cooperative Fuel Research/Removable Dome Head) standard research engine under the operating conditions defined by Christoph et al.: "Evaluation of the antiknock value of gaseous fuels by means of the methane index and their practical application in gas engines" in MTZ 33, April 1972, no. 10.

Chemical Determination of the Methane Index (by Analysis of the Composition)

Another method of determining the methane index was developed by Ryan and Callahan [RYAN et al., Journal of Engineering for Gas Turbines and Power, October 1993, vol. 115/769, and CALLAHAN et al., 18th Annual Fall Technical Conference of the ASME Internal Combustion Engine Division, 1996, ICE-vol. 27–4] and then improved by Waukesha [Selberg, CIMAC Congress 1998], who defined a new index, called the WKI index, similar to the methane index (patent U.S. Pat. No. 6,061,637).

Graphical Determination of the Methane Index

A method of calculating the methane index of a gaseous fuel from its chemical composition was established by Christoph et al. [cf. article cited above]. It consists in bringing the different constituents together into binary or ternary groups for which the methane index is given by the corresponding diagrams. The equation is of the following form:

$$MI = \frac{1}{100}\sum_{i} y_j MI_j \qquad (4)$$

where:

$MI_j$ is the methane index of the binary or tertiary group j;

$y_j$ is the concentration by volume of the mixture j in the total mixture;

MI is the methane index of the total mixture.

This equation can only be used with the ternary diagrams of each mixture group.

Also, certain rules have to be obeyed:

$MI_j$ values must not differ by more than 5 points.

At least one group must contain three components.

A group of a single component can be formed provided that the first rule applies.

The very high-knock components (for example butane) must always be included in a ternary group with antiknock components (for example methane).

The $C_5$ and higher components can be added to the butane because they are only present in the gas in trace amounts.

For mixtures having nitrogen or carbon dioxide contents below 9 and 2% respectively, the index is determined without taking these products into account. The error is less than two index points in such cases.

For higher contents, the methane index is calculated according to the following equation:

$$MI=MI(\text{without})+MI(\text{inerts})-100 \qquad (5)$$

where:

MI(without) is calculated according to equation (4);

MI(inerts) is calculated with the ternary diagram $CH_4$—$CO_2$—$N_2$, in which all the alkanes are classed as methane.

Empirical Determination of the Methane Index

1) Correlation: MI=f(NCV, $x_{CO2}$, density)

A simple equation based on measurement of the NCV, the density and the carbon dioxide content of the gas was developed by the German company Ruhrgas. This equation, which is based on a reference model (AVL program calculating the methane index from ternary diagrams), is a multiple linear regression of the following form:

$$MI=C_1+C_2.NCV+C_3.\rho+C_4.x_{CO2}+C_5.NCV.\rho+\\C_6.NCV.x_{CO2}+C_7.\rho.x_{CO2}+C_8.NCV.\rho.x_{CO2}+\\C_9.NCV^2+C_{10}.\rho^2+C_{11}.NCV^2.\rho+C_{12}.NCV.\rho^2+\\C_{13}.NCV^2.\rho.x_{CO2} \qquad (6)$$

where:

NCV is the net calorific value of the gas;

$\rho$ is the density of the gas;

$x_{CO2}$ is the carbon dioxide content.

Two further methods were developed from the calorific value or electrical permittivity data of the gas, its density and its carbon dioxide content:

The first method makes it possible to determine the composition of the gases as a function of the NCV, the density and the $CO_2$ content (calculation algorithm), allowing calculation of the methane index with the AVL program based on experimental results on a CFR engine (cf. "Evaluation of the Antiknocking Property of Gaseous Fuels by means of the Methane Number and its Practical Application to Gas Engines. ASME Paper 72-DGP-4, April 1972. Leiker M. et al.") and calculation of the NCV and the Wobbe index. The nitrogen content of the gas is estimated. The final composition of the gas is determined by an iterative calculation algorithm integrating a series of NCV second-order correlations (EP 0 939 317 A2).

The second method, which is similar to the first, makes it possible to determine the composition of the gas as a function of the electrical permittivity, the density and the carbon dioxide content of the gas. Both the nitrogen content and the NCV of the hydrocarbons are estimated. The final composition of the gas is again determined by an iterative calculation algorithm integrating a series of NCV second-order correlations (EP 1 081 494 A1).

2) Infrared Absorption

Two methods involving infrared absorption which make it possible to follow the variations in methane index are described in WO 98/25128 and WO 00/50874.

Both the empirical methods of determining the methane index afford a precision in the order of ±2 methane index points.

In addition, as these methods utilize variables (for example NCV) whose measurement can be burdensome in material and economic terms, they can only be employed for users who actually measure the NCV, the density and the carbon dioxide content of a gas (as is the case of the German company Ruhrgas, which actually measures these data in its gas distribution stations).

All the methods used to calculate the methane index and the NCV are correlations based on one, two or three physical properties. Because the approach is empirical, a progressive calibration is required to establish any kind of regression.

These techniques have real disadvantages, the first being the need to establish a strong correlation between the energy properties which it is desired to calculate and the physical properties used for this purpose. Moreover, another disadvantage of methods of this kind is that they cannot easily take account of a negative or positive effect of certain components which have a significant influence on e.g. the methane index or the NCV.

SUMMARY OF THE INVENTION

Finally, these correlations rarely allow several energy properties to be calculated simultaneously.

The present invention aims to overcome the above-mentioned disadvantages and proposes a novel method, which is simple to use, for determining at least one energy property of gases (natural gas, biogas, etc.), said method having numerous advantages, particularly the simultaneous determination of the methane index and the calorific value of gases, which are two essential characteristics for the efficient operation of gas engines used in cogeneration.

The method according to the present invention for the determination of at least one energy property of a gaseous mixture consists in:
1. measuring, on said gaseous mixture, n physical properties $\phi_i$ at a temperature T and/or one physical property $\phi_i$ at n different temperatures;
2. determining, from said physical properties, the composition of a gas with n+1 components that is equivalent to said mixture; and
3. deducing the energy properties of said gaseous mixture from said composition of the equivalent gas.

The gaseous mixture to be tested can be a gaseous fuel such as a natural gas, or a biological gas such as biogas, or a producer gas. Said mixture can consist of methane and comprise inert components such as carbon dioxide and nitrogen. As well as methane, the gaseous mixture can contain at least one other $C_2$–$C_5$ alkane, for example ethane, propane, butane or pentane. The equivalent gas can also contain hydrogen and/or carbon monoxide.

The equivalent gas can contain n+1 components, n being an integer greater than or equal to 1 and preferably equal to 2 or 3.

The physical properties considered for measurement can include the speed of sound, the thermal conductivity, the dynamic viscosity, the density, the refractive index and the dielectric constant of the gases, the infrared absorption or any other physical property of a gas at a temperature T.

The following pairs of physical properties $\phi_1$ and $\phi_2$ will preferably be used:
  dynamic viscosity and thermal conductivity;
  thermal conductivity at $T_1$ and $T_2$;
  refractive index and thermal conductivity;
  speed of sound and refractive index.

The energy properties determined can include the methane index, the calorific value, the Wobbe index and the stoichiometric air/fuel ratio.

Prior to step 1 of the method according to the invention, a calibration is carried out either by performing several series of measurements of the physical properties $\phi_i$ of an equivalent gas of known composition containing n+1 components, or by using a numerical method, for example the one described in ASTM D 25-98-68, and the relationship between said physical properties and the content of each constituent in said equivalent gas is determined.

The term "equivalent" means only that the gas containing n+1 components has the same n physical properties (same speed of sound and same thermal conductivity, for example) as the "real" gas whose energy properties are to be determined.

Thus, for example, it is advantageously possible to measure two (or three) physical properties of a gaseous mixture and, from these physical properties, to determine the composition of an equivalent ternary (or quaternary) gas.

In this case the ternary (or quaternary) diagram can be established on the basis of any triplet combination of elementary gases, for example $CH_4$—$C_2H_6$—$C_4H_{10}$ or $CH_4$—$C_2H_6$—$C_4H_{10}$—$N_2$, from measurement of any combinations of physical properties in pairs (ternary diagram) or in threes (quaternary diagram).

Advantageously, the ternary diagram will be based on the equivalent ternary composition in terms of $CH_4$—$C_2H_6$—$N_2$, $CH_4$—$C_2H_6$—$C_3H_8$, $CH_4$—$C_2H_6$—$C_4H_{10}$ or $CH_4$—$C_2H_6$—$C_4H_{10}$—$N_2$.

Real gases, such as natural gas, can generally contain up to 5 or 6 different components, or sometimes even more.

A ternary (or quaternary) diagram makes it possible to represent a gas mixture containing only three (or four) different components. Thus natural gases can be represented by a pseudo-composition or "equivalent" gas in this type of diagram.

It has been found that the real gas has the same energy properties as the equivalent gas, as determined by the two physical properties of the real gas.

DESCRIPTION OF THE PREFERRED EMBODIMENTS

Figure 1:
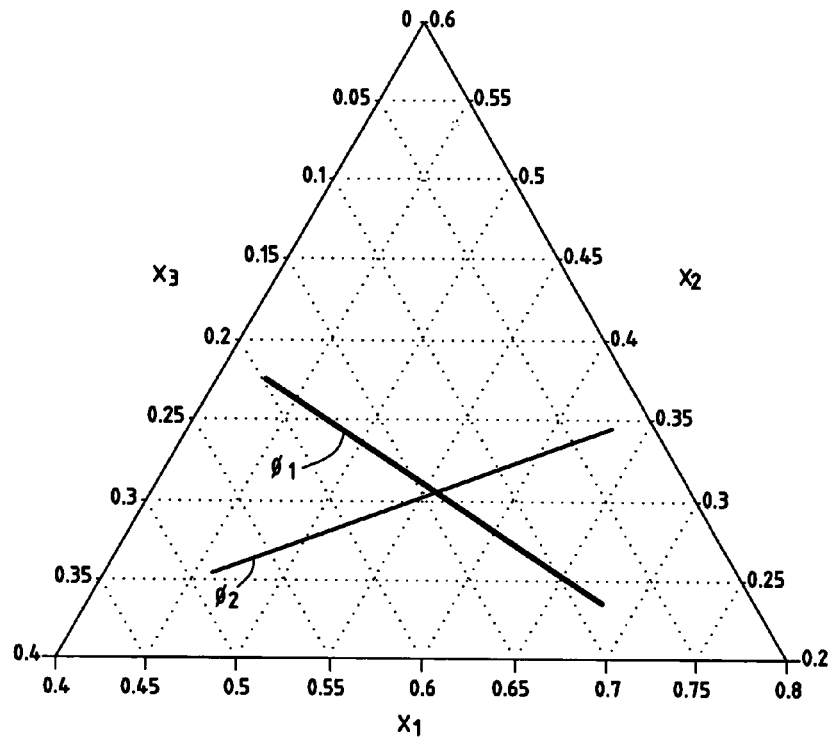
FIG. 1 is a ternary diagram in which measurements of two different physical properties are represented.

FIG. 1 shows a ternary diagram $X_1$-$X_2$-$X_3$ in which the measurements of two different physical properties will be represented.

$X_1$, $X_2$ or $X_3$ can correspond to any component of the gas, for example methane, ethane or nitrogen ($X_1+X_2+X_3=1$ or 100%).

The physical properties, identified as $\phi_1$ and $\phi_2$ in the diagram, correspond to a measurement of said physical properties. This means that the curve representative of $\phi_1$, which corresponds e.g. to a speed of sound measurement of 300 m.s$^{-1}$, represents an infinite number of different ternary compositions (a mixture of three gases or a ternary composition is always represented by one point on the diagram).

In reality there are several different mixtures which have the same speed of sound value or the same thermal conductivity value. Given that each mixture of three components is represented by one point on an equilateral triangle (ternary diagram), an infinite number of points having the same value of a physical property (speed of sound, viscosity, thermal conductivity, etc.) are ultimately obtained.

The intersection of two physical isoproperties ($\phi_1$ and $\phi_2$, constant) gives a unique ternary composition among the infinite number of compositions characterizing each of the two curves representative of $\phi_1$ and $\phi_2$.

The intersection of the two lines corresponding to the two physical properties measured gives the composition of a unique ternary mixture.

If a generalization is made by varying the physical properties $\phi_1$ and $\phi_2$ so as to encompass all the gases in question (e.g. all the natural gases), an array of almost mutually parallel lines, corresponding to different values of the physical property $\phi_i$, is obtained.

The intersection of two arrays of lines each corresponding to different values of $\phi_1$ and $\phi_2$ gives an infinite number of points that completely describe the ternary diagram.

It has been found that the coefficients $a_i$ and $b_i$ of these arrays of lines can be related to the physical properties $\phi_1$, $\phi_2$ and the temperature.

These lines are then transformed so as to be applicable in a triangular region (the coefficients are expressed as a function of $X_1$, $X_2$ and $X_3$).

Lastly, in order to characterize the whole of the ternary diagram, the content of each component of the ternary gas is finally given as a function of the physical properties ($X_1$, $X_2$ and $X_3$ are expressed as a function of the coefficients, which themselves depend on the physical properties and the temperature).

$$X_1 = f_1(X_{10}, \phi_1, \phi_2, T)$$

$$X_2 = f_2(X_{20}, \phi_1, \phi_2, T)$$

$$X_3 = 1 - X_1 - X_2$$

Here, $\phi_1$ and $\phi_2$ denote the two physical properties used to determine any gas triplet from the above equations. $X_1$, $X_2$ and $X_3$ denote the contents of the three components in the ternary gas. $X_{10}$ corresponds to the lower limit of the axis $X_1$ (0.4 on the left of FIG. 1) and $X_{20}$ corresponds to the lower limit of the axis $X_2$ (0.2 on the left of FIG. 1).

The relationships that give the triplet $X_1$, $X_2$ and $X_3$ characterize the whole of the ternary diagram. They depend on the category of gas in question (natural gas, biogas or producer gas). There is one diagram specific for biogas just as there is another diagram specific for natural gas, provided that $X_1$, $X_2$ and $X_3$ and the limits are not the same according to the category of gas in question.

On the basis of the ternary diagrams established in this way, those skilled in the art will easily be able to determine the relationships that give $X_1$, $X_2$ and $X_3$ using the conventional modeling means.

Figure 2:
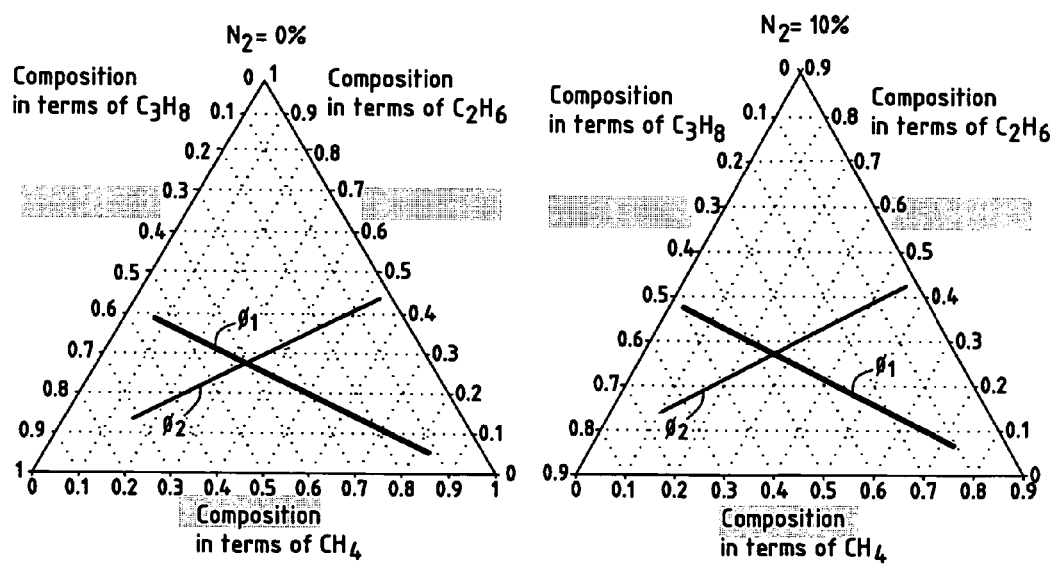
FIG. 2 is a pair of ternary diagrams in which measurements of two different physical properties are represented at two different compositions.

FIG. 2 shows an example of a ternary diagram $X_1$-$X_2$-$X_3$ in which the measurements of two different physical properties will be represented. This diagram is also indexed with the content of a fourth component $X_4$ ($X_1 \equiv CH_4$, $X_2 \equiv C_2H_6$, $X_1 \equiv C_3H_8$ and $X_4 \equiv N_2$).

This component does not appear on the diagram even though it is real. On the other hand, the sum of the components present on the diagram is no longer equal to 1 but to $1-X_4$.

This novel diagram is representative of the equivalent quaternary mixtures.

In order to characterize the whole of the ternary diagram, each ternary component is finally given as a function of the physical properties and of the fourth component $X_4$ ($X_1$, $X_2$ and $X_3$ are expressed as a function of the coefficients, which themselves depend on the physical properties and the temperature).

$$X_1 = f_1(X_{10}, \phi_1, \phi_2, X_4, T)$$

$$X_2 = f_2(X_{20}, \phi_1, \phi_2, X_4, T)$$

$$X_3 = 1 - X_1 - X_2 - X_4$$

Here, $\phi_1$ and $\phi_2$ denote the two physical properties used to determine any gas triplet from the above equations. $X_1$, $X_2$ and $X_3$ denote the contents of the three components in the ternary gas. $X_{10}$ corresponds to the lower limit of the axis $X_1$, and $X_{20}$ corresponds to the lower limit of the axis $X_2$.

Adding a constraint $X_4$ makes it necessary to measure a third physical property sensitive to $X_4$. This property must be simple to measure.

The relationships that give the quadruplet $X_1$, $X_2$, $X_3$ and $X_4$ characterize the whole of the quaternary diagram. They depend on the category of gas in question (natural gas, biogas or producer gas). They can also easily be determined by those skilled in the art using the conventional modeling means.

The use of a quaternary diagram makes it possible to improve the precision for the calculation of complicated properties such as the methane index.

This model is similar to the previous one, but integrates an additional constraint. In fact, if natural gas is taken as an example, it is possible to have a ternary diagram $CH_4$—$C_2H_6$—$C_3H_8$ whose coefficients $a_i$ and $b_i$ are indexed with the nitrogen content of the gas.

Each of the coefficients depends on the physical properties and is indexed with the nitrogen content of the gas.

Of course, the applicability of this model is conditional upon the ability to determine the nitrogen content or to determine the content of inert components (nitrogen+carbon dioxide) in the gas from a third physical property. This must be a property sensitive to nitrogen or the inert components, as is the case of the dynamic viscosity, the refractive index and the infrared absorption.

By following the procedure indicated above, it has been found that the equivalent ternary composition can be determined by means of the equations below:

$$X_1 = X_{10} + \left(1 - \frac{a_1(\varphi_1)}{\sqrt{3}}\right)\left(\frac{b_1(\varphi_1) - b_2(\varphi_2)}{a_2(\varphi_2) - a_1(\varphi_1)}\right) - \frac{b_1(\varphi_1)}{\sqrt{3}}$$

$$X_2 = X_{20} + \frac{2a_1(\varphi_1)}{\sqrt{3}}\left(\frac{b_1(\varphi_1) - b_2(\varphi_2)}{a_2(\varphi_2) - a_1(\varphi_1)} + \frac{2b_1(\varphi_1)}{\sqrt{3}}\right)$$

$$X_3 = 1 - X_1 - X_2$$

in which:

$\phi_1$ and $\phi_2$ denote the two physical properties;

$X_1$, $X_2$ and $X_3$ denote the contents of the three constituents in the ternary gas;

$X_{10}$ denotes the lower limit of the axis $X_1$;

$X_{20}$ denotes the lower limit of the axis $X_2$;

$a_1$, $b_1$, $a_2$ and $b_2$ are coefficients which depend on the physical properties.

$(\phi_1; \phi_2) = (\phi_1(T); \phi_2(T))$ for 2 different physical properties or $(\phi_1; \phi_2) = (\phi_1(T_1); \phi_1(T_2))$ for 2 temperature levels Likewise, it has been found that the equivalent quaternary compositions can be determined by means of the equations below:

$$X_1 = X_{10} + \left(1 - \frac{a_1(\varphi_1, X_4)}{\sqrt{3}}\right)\left(\frac{b_1(\varphi_1, X_4) - b_2(\varphi_2, X_4)}{a_2(\varphi_2, X_4) - a_1(\varphi_1, X_4)}\right) - \frac{b_1(\varphi_1, X_4)}{\sqrt{3}}$$

$$X_2 = X_{20} + \frac{2a_1(\varphi_1, X_4)}{\sqrt{3}}\left(\frac{b_1(\varphi_1, X_4) - b_2(\varphi_2, X_4)}{a_2(\varphi_2, X_4) - a_1(\varphi_1, X_4)}\right) - \frac{2b_1(\varphi_1, X_4)}{\sqrt{3}}$$

$$X_4 = f(\phi_3)$$

$$X_3 = 1 - X_1 - X_2 - X_4$$

in which:

$\phi_1$, $\phi_2$ and $\phi_3$ denote the three physical properties;

$X_1$, $X_2$, $X_3$ and $X_4$ denote the contents of the four constituents in the quaternary gas;

$X_{10}$ denotes the lower limit of the axis $X_1$;

$X_{20}$ denotes the lower limit of the axis $X_2$;

$a_1$, $b_1$, $a_2$ and $b_2$ are coefficients which depend on the physical properties.

$(\phi_1; \phi_2) = (\phi_1(T); \phi_2(T))$ for 2 different physical properties or $(\phi_1; \phi_2) = (\phi_1(T_1); \phi_1(T_2))$ for 2 new temperature levels The calculation of certain energy properties of natural gas follows logically from the ternary or quaternary diagrams. This is the case of the net calorific value (NCV) of the gas, the stoichiometric air/fuel ratio (SAFR) or the Wobbe index, which is very important for those in the gas industry. These properties depend directly on the composition of the gas in question. The methane index also depends on the composition, but indirectly. However, it is possible to use a calculation software of the AVL type for this purpose.

It is thus possible to produce a sensor capable of following the variations in the NCV, the SAFR and the Wobbe index of natural gas or any other gas (biogas, producer gas) simply by measuring two different physical properties. It is also possible to determine the methane index of these gases.

In the case of natural gas and biogas, measurement of the thermal conductivity at two temperature levels makes it possible to follow the variations in the NCV of these gases with good precision in the ternary or quaternary diagram described above.

Likewise, measurement of the refractive index combined with measurement of the thermal conductivity or the speed of sound makes it possible to obtain the ternary or quaternary composition resulting from the method. The energy properties of this composition, such as the methane index, the NCV or the Wobbe index, can be determined.

Measurement of the viscosity of the gas combined with any other physical property is very appropriate for this methodology.

Thus the present invention further relates to a device for carrying out the method according to the invention, said device comprising:

at least n sensors for measuring the physical properties $\phi_i$;

an electronic module for determining the composition of the equivalent ternary (or quaternary) gas and the desired energy properties.

The choice of physical properties depends on the type of ternary diagram and on the fact that certain physical properties may or may not be strongly correlated with one another.

Figure 3:
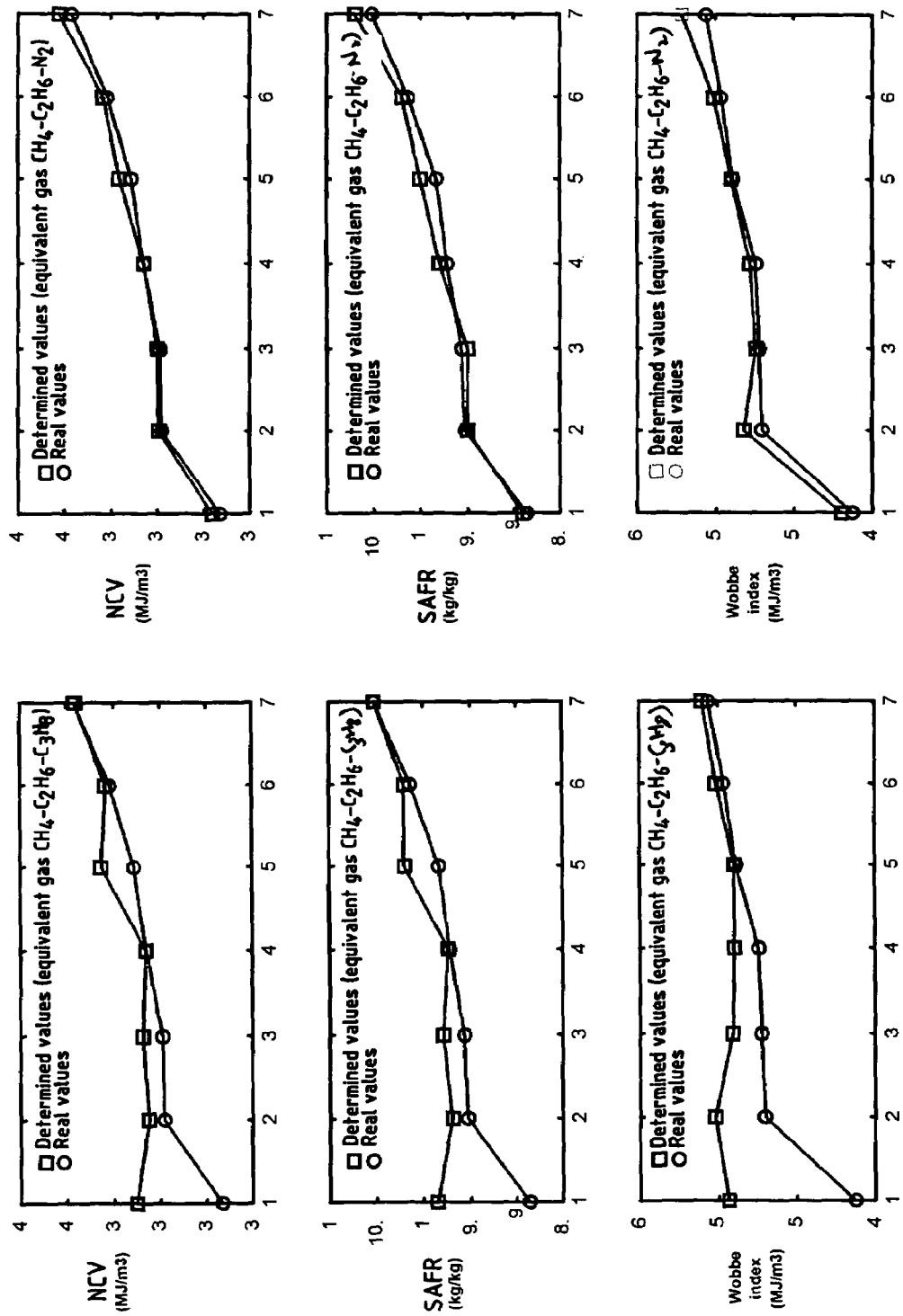
FIG. 3 is a series of plots comparing real values of physical properties with values determined according to the invention.

The method according to the invention is applicable to all natural gases of diverse origins, as proved by the results given in FIG. 3, which represent the real energy properties (NCV, Wobbe index and stoichiometric air/fuel ratio) and those obtained by the method of the invention for natural gases having the following compositions:

the thermal conductivity and the refractive index or the speed of sound and the refractive index in the case of the, ternary gas $CH_4$—$C_2H_6$—$N_2$.

The method of the invention makes it possible to determine the physical properties of a gaseous mixture with a mean deviation in the order of 1%.

The invention claimed is:

1. Method of determining at least one energy property of a gaseous mixture, comprising the steps of:
   a) measuring, on said gaseous mixture, n physical properties $\phi_i$ at a temperature T and/or one physical property $\phi_i$ at n different temperatures;
   b) determining, from said physical properties, the composition of a gas with n+1 components that is equivalent to said mixture; and
   c) deducing the energy properties of said gaseous mixture from said composition of the equivalent gas.

2. Method according to claim 1, wherein the physical properties $\phi_i$ are selected from the group consisting of speed of sound, the thermal conductivity, the dynamic viscosity, the density, the refractive index, the dielectric constant of the gases, and the infrared absorption.

3. Method according to claim 1, wherein the gaseous mixture is selected from the group consisting of natural gases, biogas and producer gases.

4. Method according to claim 1, wherein the components of the equivalent gas are selected from the group consisting of methane, $C_2$–$C_5$ alkanes, nitrogen, inert components, hydrogen and carbon monoxide.

5. Method according to claim 1, wherein the gaseous mixture is a natural gas or a biogas and in that the equivalent gas is a ternary gas consisting of methane and two $C_2$–$C_5$ alkanes or of methane, one $C_2$–$C_5$ alkane and nitrogen or inert components.

6. Method according to claim 1, wherein the equivalent gas is a quaternary gas consisting of methane, two $C_2$–$C_5$ alkanes and nitrogen or inert components.

7. Method according to claim 1, wherein the physical properties $\phi_i$ measured are $\phi_1$ and $\phi_2$, selected respectively from the group consisting of:

the dynamic viscosity and the thermal conductivity;

TABLE 2

| | Composition of natural gases | | | | | |
|---|---|---|---|---|---|---|
| FRANCE | ALGERIA | | NORTH | NORWAY | | HOLLAND |
| LACQ (1) | SKIKDA (2) | ARZEW (3) | AMERICA (4) | EKOFISK (5) | RUSSIA (6) | GRONINGEN (7) |
| $CH_4$ | 97.3 | 91.2 | 88.6 | 94.69 | 88.2 | 96.2 | 83.5 |
| $C_2H_6$ | 2.1 | 6.5 | 8.2 | 2.58 | 5.4 | 1.2 | 3.6 |
| $C_3H_8$ | 0.2 | 1.1 | 2 | 0.2 | 1.2 | 0.3 | 0.7 |
| $C_4H_{10}$ | 0.1 | 0.2 | 0.6 | 0.06 | 0.4 | 0.1 | 0.2 |
| $C_5H_{12}$ | 0 | 0 | 0 | 0.03 | 0.2 | 0.1 | 0.1 |
| $N_2$ | 0.3 | 1 | 0.6 | 1.63 | 3.2 | 1.8 | 10.8 |
| $CO_2$ | 0 | 0 | 0 | 0.81 | 1.4 | 0.3 | 1.1 |

The ternary gases used in these experiments were respectively the ternary gases $CH_4$—$C_2H_6$—$C_3H_8$ and $CH_4$—$C_2H_6$—$N_2$ and the physical properties $\phi_1$ and $\phi_2$ were respectively as follows:

the thermal conductivity and the refractive index in the case of the ternary gas $CH_4$—$C_2H_6$—$C_3H_8$;

the thermal conductivity at temperatures $T_1$ and $T_2$;

the refractive index and the thermal conductivity;

the speed of sound and the refractive index.

8. Method according to claim 1, wherein, prior to step a), a calibration is carried out either by performing several series of measurements of the physical properties $\phi_i$ of an equivalent gas of known composition containing n+1 components, or by using a numerical method, and the relationship between said physical properties and the content of each constituent in said equivalent gas is determined.

9. Method according to claim 1, wherein the composition of the equivalent ternary mixture is determined in a ternary diagram by means of the equations below:

$$X_1 = X_{10} + \left(1 - \frac{a_1(\varphi_1)}{\sqrt{3}}\right)\left(\frac{b_1(\varphi_1) - b_2(\varphi_2)}{a_2(\varphi_2) - a_1(\varphi_1)}\right) - \frac{b_1(\varphi_1)}{\sqrt{3}}$$

$$X_2 = X_{20} + \frac{2a_1(\varphi_1)}{\sqrt{3}}\left(\frac{b_1(\varphi_1) - b_2(\varphi_2)}{a_2(\varphi_2) - a_1(\varphi_1)} + \frac{2b_1(\varphi_1)}{\sqrt{3}}\right)$$

$$X_3 = 1 - X_1 - X_2$$

in which:

$\phi_1$ and $\phi_2$ denote the two physical properties;

$X_1$, $X_2$ and $X_3$ denote the contents of the three constituents in the ternary gas;

$X_{10}$ denotes the lower limit of the axis $X_1$;

$X_{20}$ denotes the lower limit of the axis $X_2$;

$a_1$, $b_1$, $a_2$ and $b_2$ are coefficients which depend on the physical properties;

$(\phi_1; \phi_2) = (\phi_1(T); \phi_2(T))$ for 2 different physical properties or $(100_1; \phi_2) = (\phi_1(T_1); \phi_1(T_2))$ for 2 temperature levels.

10. Method according to claim 1, wherein the composition of the equivalent quaternary mixture is determined by means of the equations below:

$$X_1 = X_{10} + \left(1 - \frac{a_1(\varphi_1, X_4)}{\sqrt{3}}\right)\left(\frac{b_1(\varphi_1, X_4) - b_2(\varphi_2, X_4)}{a_2(\varphi_2, X_4) - a_1(\varphi_1, X_4)}\right) - \frac{b_1(\varphi_1, X_4)}{\sqrt{3}}$$

$$X_2 = X_{20} + \frac{2a_1(\varphi_1, X_4)}{\sqrt{3}}\left(\frac{b_1(\varphi_1, X_4) - b_2(\varphi_2, X_4)}{a_2(\varphi_2, X_4) - a_1(\varphi_1, X_4)}\right) - \frac{2b_1(\varphi_1, X_4)}{\sqrt{3}}$$

$$X_4 = f(\phi_3)$$

$$X_3 = 1 - X_1 - X_2 - X_4$$

in which:

$\phi_1$, $\phi_2$ and $\phi_3$ denote the three physical properties;

$X_1$, $X_2$, $X_3$ and $X_4$ denote the contents of the four constituents in the quaternary gas;

$X_{10}$ denotes the lower limit of the axis $X_1$;

$X_{20}$ denotes the lower limit of the axis $X_2$;

$a_1$, $b_1$, $a_2$ and $b_2$ are coefficients which depend on the physical properties $(\phi_1; \phi_2) = (\phi_1(T); \phi_2(T))$ for 2 different physical properties or $(\phi_1; \phi_2) = (\phi_1(T_1); \phi_2(T_2))$ for 2 new temperature levels.

11. Method according to claim 1, wherein the methane index, the Wobbe index, the net calorific value or the stoichiometric air/fuel ratio is determined.

12. Device for carrying out the method according to claim 1, comprising:

at least n sensors for measuring the physical properties $\phi_i$; and an electronic module for determining the composition of the equivalent gas and the desired energy properties.

* * * * *